(12) United States Patent
Beden et al.

(10) Patent No.: US 7,488,301 B2
(45) Date of Patent: Feb. 10, 2009

(54) METHOD FOR RETURNING BLOOD FROM A BLOOD TREATMENT DEVICE, AND DEVICE FOR CARRYING OUT THIS METHOD

(75) Inventors: Josef Beden, Mainz-Kastel (DE); Joachim Manke, Löhnberg (DE)

(73) Assignee: Fresenius Medical Care Deutschland GmbH, Bad Homburg v.d.H (DE)

( * ) Notice: Subject to any disclaimer, the term of this patent is extended or adjusted under 35 U.S.C. 154(b) by 242 days.

(21) Appl. No.: 10/527,460

(22) PCT Filed: Jul. 22, 2003

(86) PCT No.: PCT/EP03/08000

§ 371 (c)(1),
(2), (4) Date: Mar. 11, 2005

(87) PCT Pub. No.: WO2004/033001

PCT Pub. Date: Apr. 22, 2004

(65) Prior Publication Data

US 2006/0079826 A1 Apr. 13, 2006

(30) Foreign Application Priority Data

Sep. 11, 2002 (DE) ................ 102 42 008
Sep. 30, 2002 (DE) ................ 102 45 619

(51) Int. Cl.
*A61M 37/00* (2006.01)
*C02F 1/44* (2006.01)

(52) U.S. Cl. ............... 604/6.09; 604/4.01; 604/5.01; 604/6.1; 604/6.11; 210/645

(58) Field of Classification Search ............... 604/4.01, 604/5.01, 5.04, 6.09, 6.1, 6.11, 65, 67; 422/44; 210/600, 634, 645–647, 649, 650, 739, 745, 210/195.2, 433.1, 500.21, 416.1
See application file for complete search history.

(56) References Cited

U.S. PATENT DOCUMENTS

| 3,898,017 | A | * | 8/1975 | Mandroian ............ 417/65 |
| 4,770,769 | A | * | 9/1988 | Schael ............ 210/96.2 |
| 5,470,483 | A | * | 11/1995 | Bene et al. ............ 210/741 |
| 5,783,072 | A | * | 7/1998 | Kenley et al. ............ 210/195.2 |
| 6,132,616 | A | * | 10/2000 | Twardowski et al. ......... 210/646 |
| 2006/0237351 | A1 | * | 10/2006 | Felding ............ 210/101 |
| 2006/0254982 | A1 | * | 11/2006 | Kopperschmidt .......... 210/646 |

FOREIGN PATENT DOCUMENTS

| DE | 42 40 681 A1 | 6/1994 |
| DE | 197 04 564 A1 | 8/1998 |
| DE | 100 11 208 C1 | 9/2001 |
| DE | 102 24 750 A1 | 12/2003 |
| EP | 0 578 175 B1 | 1/1994 |
| WO | WO 01/51106 A1 | 7/2001 |

* cited by examiner

*Primary Examiner*—Leslie R Deak
(74) *Attorney, Agent, or Firm*—Jacobson Holman PLLC

(57) ABSTRACT

A method for the return of blood from a blood treatment apparatus, preferably from a dialysis apparatus, uses a pumped substituate fluid to displace the blood. A substituate pump contained in the treatment apparatus displaces the blood by means of the correspondingly transported substituate fluid until it is detected in corresponding detectors that substituate fluid is flowing back in the line instead of blood. Once the transported substituate fluid has been detected, the blood volume is further displaced in a controlled manner until it has reached the line outlet of the corresponding line.

21 Claims, 1 Drawing Sheet

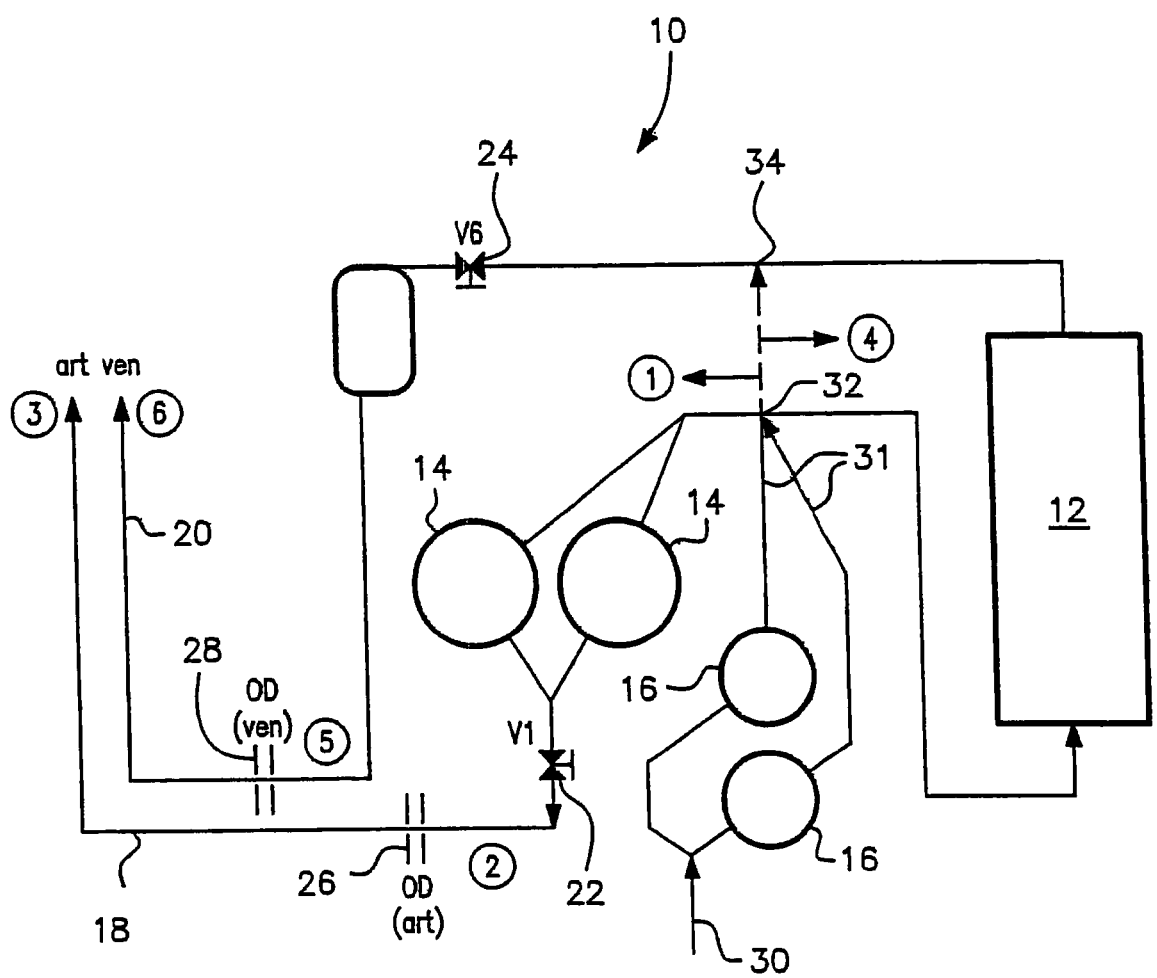

METHOD FOR RETURNING BLOOD FROM A BLOOD TREATMENT DEVICE, AND DEVICE FOR CARRYING OUT THIS METHOD

This is a nationalization of PCT/EP03/008000 filed Jul. 22, 2003 and published in German.

BACKGROUND OF THE INVENTION

1. Field of Invention

The invention relates to a method for the return of blood from a blood treatment apparatus, preferably a dialysis apparatus, and to an apparatus to carry out the method.

2. Description of the Prior Art

Dialysis apparatus of the most varied construction for different applications are known as blood treatment apparatus. An extracorporeal blood circuit is thus provided, for example for hemodiafiltration (HDF), comprising the following components: comprising a dialyzer, at least two lines with outlets (patient needles), a blood pump, a dialysate pump, a first valve arranged in the first line, a second valve arranged in the second line and a predilution port or a postdilution port for the feeding of the substituate fluid.

The individual components can be assembled in differential construction. However, these corresponding components are particularly advantageously components of an integrated cassette such as was described, for example, in DE 102 24 750.1 of Jun. 4, 2002.

The problem results at the end of a dialysis session that the blood present in the extracorporeal circuit is returned to the patient as completely as possible. Appropriate methods are already known for the different blood treatment apparatus for this purpose. A method for the return of blood from a blood treatment apparatus is described, for example, in EP 0 578 175 B1 while citing further alternative methods.

Starting from the known methods for the return of blood from a blood treatment apparatus, a procedure for a return of blood which is as quantitative as possible should be developed which is designed to be even further simplified and more expedient where possible.

SUMMARY OF THE INVENTION

The object is solved in a system with a predilution port in a method in which a substituate fluid displaces blood in a volume-controlled manner from a first line and from a blood treatment element and a second line. The object is solved with an apparatus having a postdilution port by a method in which the substituate fluid displaces blood in a volume-controlled manner from the blood treatment element and the first line and from the second line.

Accordingly, the method for the return of blood in accordance with the first solution of the invention is carried out with the following steps in a blood treatment apparatus comprising a blood treatment element, two lines with outlets, a blood pump, a first valve arranged in the first line, a second valve arranged in the second line and a predilution port for the feeding of the substituate fluid, comprising a substituate supply line which is connected to the predilution port and in which a substituate pump is interposed:

the first valve in the first line is opened and the second valve arranged in the second line is closed;

the blood pump is set to feedthrough or it is also running while the substituate pump displaces the blood by means of transported substituate fluid;

the blood is further displaced in a volume-controlled manner until it has reached the line outlet of the first line;

the blood pump is closed or stopped, the first valve is closed and the second valve is opened;

the substituate pump displaces blood through the released second line and the blood treatment element by transported substituate fluid; and the blood is further displaced in a volume-controlled manner until it has reached the line outlet of the second line.

In accordance with the second solution of the invention, the method for the return of blood is carried out with the following steps in a blood treatment apparatus comprising a blood treatment element, two lines with outlets, a blood pump, a first valve arranged in the first line, a second valve arranged in the second line and a postdilution port for the feeding of the substituate fluid, comprising a substituate supply line which is connected to the postdilution port and in which a substituate pump is interposed:

the first valve in the first line is opened and the second valve arranged in the second line is closed;

the blood pump is set to feedthrough or it is also running while the substituate pump displaces the blood through the blood treatment element and the first line by means of transported substituate fluid;

the blood is further displaced in a volume-controlled manner until it has reached the line outlet of the first line;

the blood pump is closed or stopped, the first valve is closed and the second valve is opened;

the substituate pump displaces blood through the released second line by transported substituate fluid; and the blood is further displaced in a volume-controlled manner until it has reached the line outlet of the second line.

The solutions of the invention permit a return of blood equally arterially or venously. In contrast to the standard method with arterial disconnection and subsequent venous disconnection, the disconnection of the patient is only necessary right at the end of the return procedure. Then, the arterial inlet is first disconnected and connected to a flushing solution bag containing physiological saline. The blood in the hose system is then returned to the patient via the venous connection with the aid of the blood pump. The return is monitored manually in this process.

A change-around of the patient connections for the start of the return is not necessary with the method in accordance with the invention.

The substituate pump is particularly advantageously used for the supply of fluid, whereby a good separation boundary results between the added solution and the blood.

In accordance with a preferred aspect of the invention, a membrane pump with highly precise dosing is used as the substituate pump. In cooperation with the two optical sensors, this permits a very effective return of blood at a precise point since the residual volume in the lines from the sensors to the line outlet is known and this known volume can be displaced at a precise point from the line by a corresponding control of the membrane pump with highly precise dosing.

Advantageous further developments of the method result from the other embodiments of the invention described herein.

The invention finally relates to an apparatus that includes a blood treatment element, a blood pump, a substituate pump, a first line as an arterial blood line, a second line as a venous blood line, valves, and a control apparatus. Advantageous aspects of this apparatus result from the various embodiments thereof that are described herein.

BRIEF DESCRIPTION OF THE DRAWINGS

Further details, features and advantages of the invention will be explained with reference to an embodiment shown in the drawing. The only FIGURE shows a basic circuit diagram of an online hemodiafiltraton apparatus with which the method in accordance with the invention can be carried out.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to these skilled in the art from this detailed description.

The dialysis apparatus 10 shown in the FIGURE contains a dialyzer 12, a blood pump 14 which is made as a membrane pump, a substituate pump 16 which is likewise made as a membrane pump, a first line 18 as an arterial blood line and a second line 20 as a venous blood line. A first valve 22 is arranged upstream of the blood pump 14 in the transport direction in the first line 18 during a blood treatment. Both the blood pump 14 and the substituate pump 16 are made as double pumps connected in parallel, which permits an almost uniform transport. A second valve 24 is arranged in the second line 20. A first optical detector 26 is arranged in the first line and a second optical detector 28 is arranged in the second line.

The substituate pump 16 transports substituate solution from a substituate source 30 via a substituate supply line 31 either to a predilution port 32 or to a postdilution port 34. The substituate source 30 can be a bag with a suitable fluid or a preparation unit inside the dialysis apparatus 10 which prepares a suitable fluid on site.

In the event that the substituate pump 16 transports the substituate to a predilution port 32, the first valve 22 in the first line 18 is opened and the second valve 24 in the second line 20 is closed after the end of the dialysis for the return of blood from the dialysis apparatus 10 to the patient (not shown in any more detail here). The blood is very largely pressed out of the blood pump 14. The blood pump 14 is set to feedthrough or it is preferably also running under pressure control while the substituate pump 16 displaces blood in the line 18 contrary to the normal direction of flow by means of transported substituate fluid until it is detected in the first optical detector 26 that substituate fluid is flowing back instead of blood. This is recognized by the optical detector in that the substituate fluid is much lighter with respect to blood.

From this moment in time, the blood is further displaced in a volume-controlled manner until it has reached the line outlet of the first line. The volume in the residual line behind the first detector 26 up to the line outlet is precisely known and the desired volume can be precisely displaced by means of the highly precisely dispensing substituate pump 16. After the displacement of the volume portion of blood, the arterial blood is very largely led back to the patient in a quantitative manner.

To return the venous blood, the blood pump is now closed or stopped and the first valve 22 is closed, while the second valve 24 is opened. The substituate pump now displaces blood through the released second line 20 and through the dialyzer 12 via transported substituate fluid until it is detected in the second detector 28 that substituate fluid is flowing back instead of blood. The blood is now again further displaced in a volume-controlled manner until it has reached the line outlet of the second line so that the venous blood has now also been returned to the patient.

If the substituate fluid is now not added through the prediiution port 32, but through the postdilution port 34, the method described above is modified in that the substituate solution already runs through the dialyzer 12 on the displacement of the arterial blood and displaces the corresponding blood, as well as the blood in the line 18 following after, in the manner described above.

The previously shown order of emptying the first line 18 and subsequently emptying the second line 20 can naturally also be swapped over within the framework of the invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for the return of blood from a blood treatment apparatus that includes a blood treatment element configured for hemodiafiltration, a first line and a second line each having an outlet, a blood pump, a first valve arranged in the first line, a second valve arranged in the second line, and a predilution port configured to feed a substituate fluid, with a substituate supply line connected to the predilution port and to a substitutate pump, the method comprising the steps of:

opening the first valve in the first line and closing the second valve in the second line;

configuring the blood pump for feedthrough operation or pressure control operation and operating the substituate pump to displace the blood with transported substituate fluid in a volume-controlled manner until the displaced blood has reached the first line outlet;

discontinuing operation of the blood pump, closing the first valve, and opening the second valve; and operating the substituate pump to displace the blood through the second line and the blood treatment element with transported substituate fluid in a volume-controlled manner until the displaced blood has reached the second line outlet.

2. A method for the return of blood from a blood treatment apparatus that includes a blood treatment element configured for hemodiafiltration, a first line and a second line each having an outlet, a blood pump, a first valve arranged in the first line, a second valve arranged in the second line, and a postdilution port configured to feed a substituate fluid, with a substituate supply line connected to the postdilution port and to a substitutate pump, the method comprising the steps of:

opening the first valve in the first line and closing the second valve in the second line;

configuring the blood pump for feedthrough operation or pressure control operation and operating the substituate pump to displace the blood through the blood treatment element and the first line with transported substituate fluid in a volume-controlled manner until the displaced blood has reached the first line outlet;

discontinuing operation of the blood pump, closing the first valve, and opening the second valve; and operating the substituate pump to displace the blood through the second line with transported substituate fluid in a volume-controlled manner until the displaced blood has reached the second line outlet.

3. The method in accordance with claim 1, wherein the step of pumping the substituate fluid includes using a membrane pump.

4. The method in accordance with claim 1, wherein the blood treatment element is a dialyzer in the hemodiafiltration.

5. The method in accordance with claim 1, wherein the blood treatment element is a hemofilter in the hemodiafiltration.

6. The method in accordance with claim 1, further comprising a step of detecting the flow of the transported substituate fluid.

7. The method in accordance with claim 6, wherein the step of detecting uses optical detectors.

8. The method in accordance with claim 1, wherein the step of displacing the blood from the blood pump with the substituate fluid includes displacing substantially all of the blood therefrom.

9. An apparatus for carrying out a method in accordance with claim 1, comprising a blood treatment element configured for hemodiafiltration, a blood pump, a substituate fluid pump, a first line as an arterial blood line, a second line as a venous blood line, valves that control flow in the first and second lines, and a control apparatus.

10. The apparatus in accordance with claim 9, further comprising detectors arranged in the lines that detect the flow of the substituate fluid.

11. The apparatus in accordance with claim 9, wherein each of the pumps is configured as double pumps connected in parallel.

12. The method according to claim 1, wherein the predilution port is located downstream of the blood pump and upstream of the blood treatment element.

13. The method according to claim 2, wherein the postdilution port is located downstream of the blood treatment element and upstream of the second valve.

14. The method according to claim 1, wherein the first line and the second line are used both as conduits for transport of blood during operation of the blood treatment element and as conduits for the return of the displaced blood from the blood treatment apparatus.

15. The method according to claim 2, wherein the first line and the second line are used both as conduits for transport of blood during operation of the blood treatment element and as conduits for the return of the displaced blood from the blood treatment apparatus.

16. The apparatus according to claim 10, wherein the detectors are optical detectors.

17. A method of removing blood from a blood treatment apparatus that includes a blood treatment element configured for hemodiafiltration, a first line and a second line each having an outlet, a blood pump, a first valve disposed in the first line, a second valve disposed in the second line, a substitutate pump that feeds a substituate fluid, a predilution port and a postdilution port each configured to distribute the substituate fluid, and a substituate supply line that is connectable to the predilution port and to the postdilution port, the method comprising the steps of:

in a predilution mode, opening the first valve in the first line and closing the second valve in the second line;

configuring the blood pump for feedthrough operation or pressure control operation and operating the substituate pump to feed the substituate fluid through the predilution port to displace the blood with transported substituate fluid in a volume-controlled manner until the displaced blood has reached the first line outlet;

discontinuing operation of the blood pump, closing the first valve, and opening the second valve; and operating the substituate pump to displace the blood through the second line and the blood treatment element with transported substituate fluid in a volume-controlled manner until the displaced blood has reached the second line outlet; and in a postdilution mode, opening the first valve in the first line and closing the second valve in the second line;

configuring the blood pump for feedthrough operation or pressure control operation and operating the substituate pump to feed the substituate fluid through the postdilution port to displace the blood through the blood treatment element and the first line with transported substituate fluid in a volume-controlled manner until the displaced blood has reached the first line outlet;

discontinuing operation of the blood pump, closing the first valve, and opening the second valve; and operating the substituate pump to displace the blood through the second line with transported substituate fluid in a volume-controlled manner until the displaced blood has reached the second line outlet.

18. The method according to claim 17, wherein the step of displacing the blood with transported substituate fluid in a volume-controlled manner includes using a membrane substitutate pump.

19. The method according to claim 17, wherein the step of displacing the blood with transported substituate fluid in a volume-controlled manner includes detecting the flow of the transported substituate fluid with an optical detector.

20. The method according to claim 17, wherein the predilution port is located downstream of the blood pump.

21. An apparatus for carrying out a method in accordance with claim 2, comprising a blood treatment element configured for hemodiafiltration, a blood pump, a substituate fluid pump, a first line as an arterial blood line, a second line as a venous blood line, valves that control flow in the first and second lines, and a control apparatus.

* * * * *